United States Patent
Fujioka et al.

(10) Patent No.: US 11,402,368 B2
(45) Date of Patent: Aug. 2, 2022

(54) BIOLOGICAL SAMPLE ANALYZER AND BIOLOGICAL SAMPLE ANALYSIS METHOD

(71) Applicant: Hitachi High-Technologies Corporation, Tokyo (JP)

(72) Inventors: Michiru Fujioka, Tokyo (JP); Nobuyuki Isoshima, Tokyo (JP); Wataru Sato, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 362 days.

(21) Appl. No.: 15/772,196

(22) PCT Filed: Nov. 24, 2015

(86) PCT No.: PCT/JP2015/082903
§ 371 (c)(1),
(2) Date: Apr. 30, 2018

(87) PCT Pub. No.: WO2017/090087
PCT Pub. Date: Jun. 1, 2017

(65) Prior Publication Data
US 2018/0313813 A1    Nov. 1, 2018

(51) Int. Cl.
*G01N 33/487* (2006.01)
*C12Q 1/6816* (2018.01)
(Continued)

(52) U.S. Cl.
CPC ..... *G01N 33/48721* (2013.01); *C12Q 1/6816* (2013.01); *C12Q 1/6869* (2013.01);
(Continued)

(58) Field of Classification Search
CPC ............ C12Q 1/6869; C12Q 2565/607; C12Q 2565/631; C12Q 1/6816; C12Q 1/686;
(Continued)

(56) References Cited

U.S. PATENT DOCUMENTS

| 2005/0074782 A1* | 4/2005 | Krishnan ............... C12Q 1/686 435/6.11 |
| 2011/0162963 A1 | 7/2011 | Hibbs et al. |

(Continued)

FOREIGN PATENT DOCUMENTS

| JP | 2014-519823 A | 8/2014 |
| JP | 2015-206737 A | 11/2015 |

(Continued)

OTHER PUBLICATIONS

Nicoli et al., "DNA Translocations through Solid-State Plasmonic Nanopores", Nano Letters, vol. 14, 2014, pp. 6917-6925.
(Continued)

*Primary Examiner* — Lydia Edwards
(74) *Attorney, Agent, or Firm* — Crowell & Moring LLP

(57) ABSTRACT

A biological sample analyzer using a nanopore, said analyzer comprising: a first chamber that storing a solvent; a baseboard provided with a nanopore through which a biological sample passes; a second chamber which is positioned adjacently to the first chamber via the baseboard and stores the solvent; a first electrode formed in the first chamber; a second electrode formed in the second chamber; a detector detecting the biological sample which has passed through the nanopore; and a stirrer stirring the solvent in the first chamber.

12 Claims, 5 Drawing Sheets

(51) Int. Cl.
*C12Q 1/686* (2018.01)
*C12Q 1/6869* (2018.01)
*B82Y 5/00* (2011.01)
*B82Y 15/00* (2011.01)

(52) U.S. Cl.
CPC ............... *B82Y 5/00* (2013.01); *B82Y 15/00* (2013.01); *C12Q 1/686* (2013.01); *C12Q 2563/159* (2013.01); *C12Q 2565/629* (2013.01)

(58) Field of Classification Search
CPC ........ C12Q 2563/159; C12Q 2565/629; B82Y 15/00; B82Y 5/00; G01N 33/48721
See application file for complete search history.

(56) References Cited

U.S. PATENT DOCUMENTS

| | | |
|---|---|---|
| 2013/0264206 A1 | 10/2013 | Eom et al. |
| 2014/0262784 A1 | 9/2014 | Clarke et al. |
| 2015/0060276 A1 | 3/2015 | Golovchenko et al. |
| 2016/0153960 A1 | 6/2016 | Kato et al. |

FOREIGN PATENT DOCUMENTS

| | | |
|---|---|---|
| WO | WO 2014/165168 A1 | 10/2014 |
| WO | WO 2014/208184 A1 | 12/2014 |

OTHER PUBLICATIONS

International Search Report (PCT/ISA/210) issued in PCT Application No. PCT/JP2015/082903 dated Feb. 16, 2016 with English-language translation (five (5) pages).

Japanese-language Written Opinion (PCT/ISA/237) issued in PCT Application No. PCT/JP2015/082903 dated Feb. 16, 2016 (five (5) pages).

Belkin et al., "Stretching and Controlled Motion of Single-Stranded DNA in Locally Heated Solid-State Nanopores", ACS Nano, vol. 7, Jul. 22, 2013, pp. 6816-6824.

He et al., "Thermophoretic Manipulation of DNA Translocation through Nanopores", ACS Nano, vol. 7, Dec. 2, 2012, pp. 538-546.

* cited by examiner

[Fig. 1]
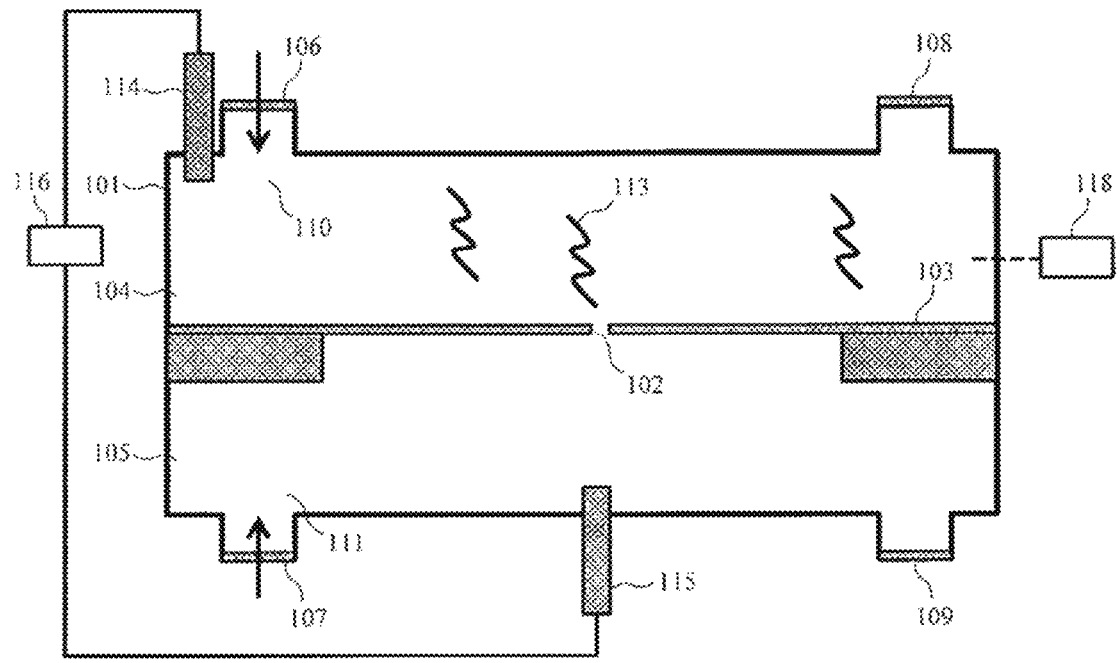
[Fig. 2]
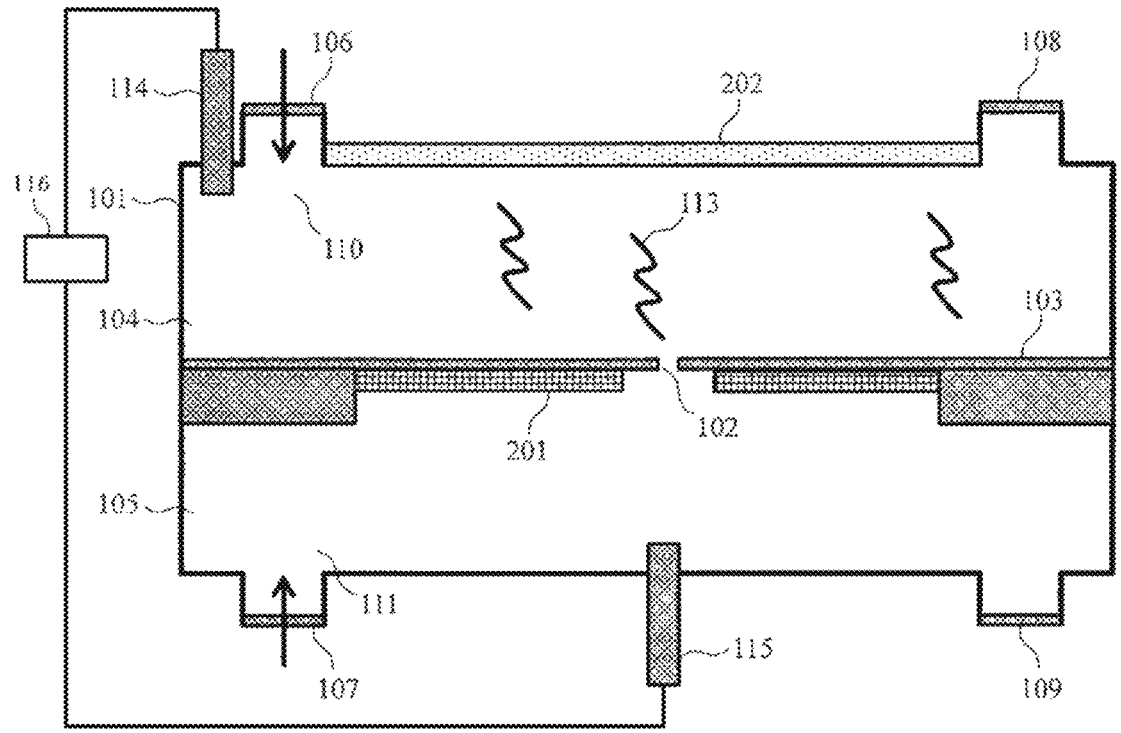

[Fig. 3]
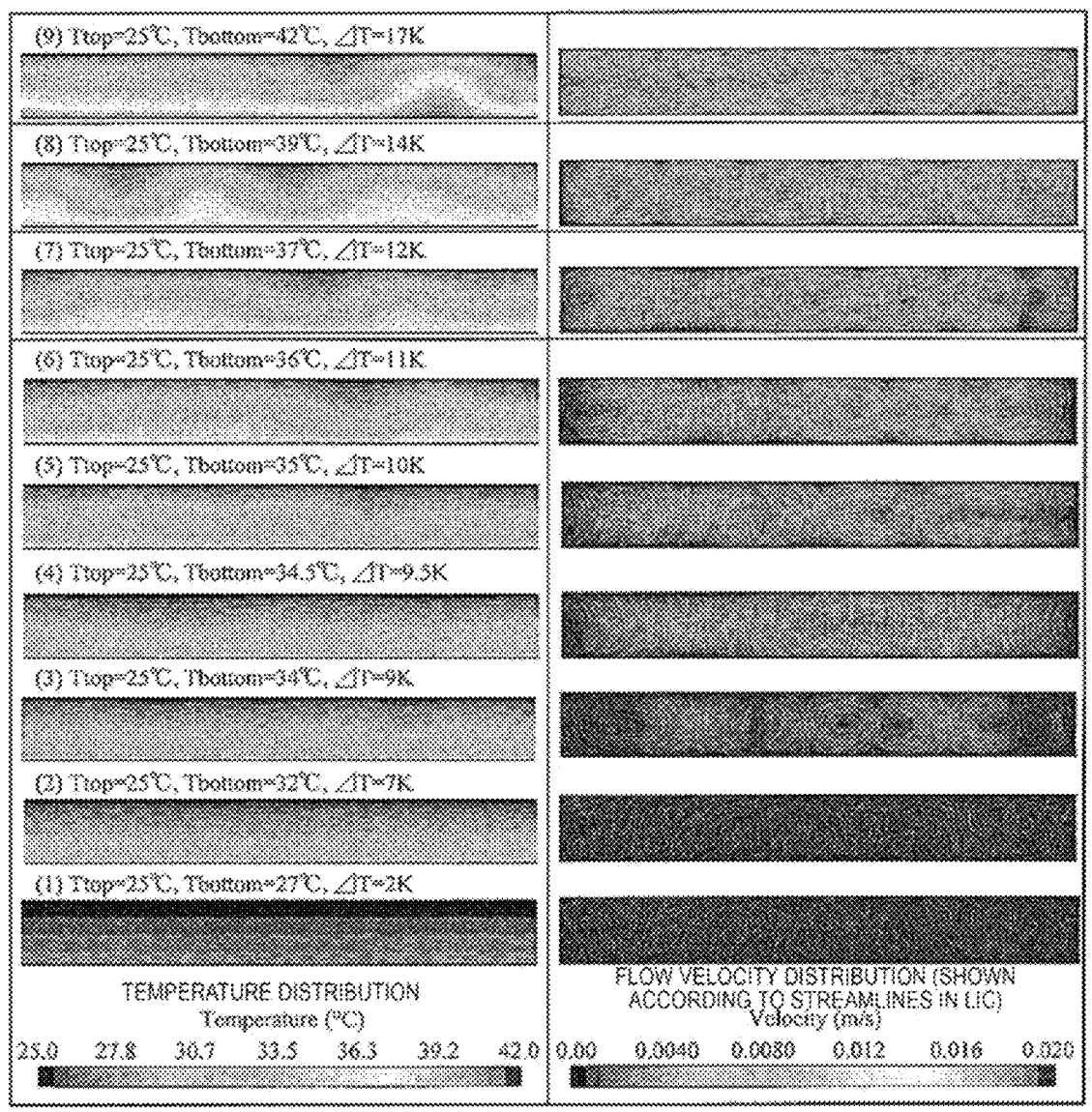

[Fig. 4]
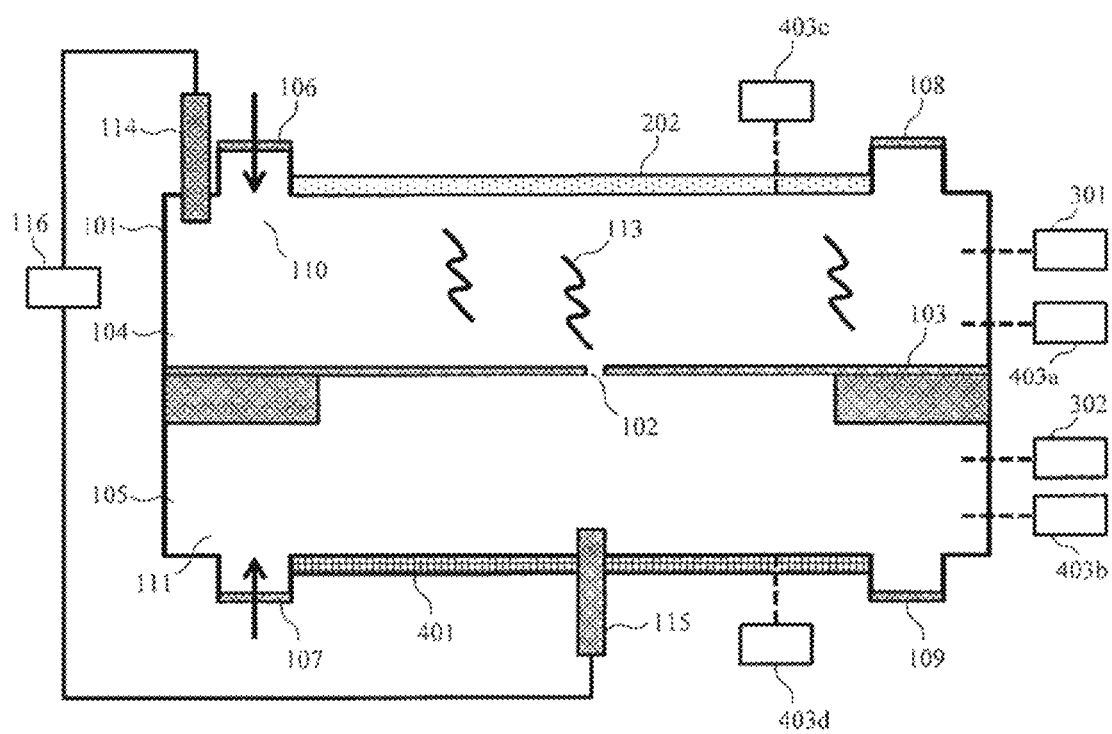
[Fig. 5]
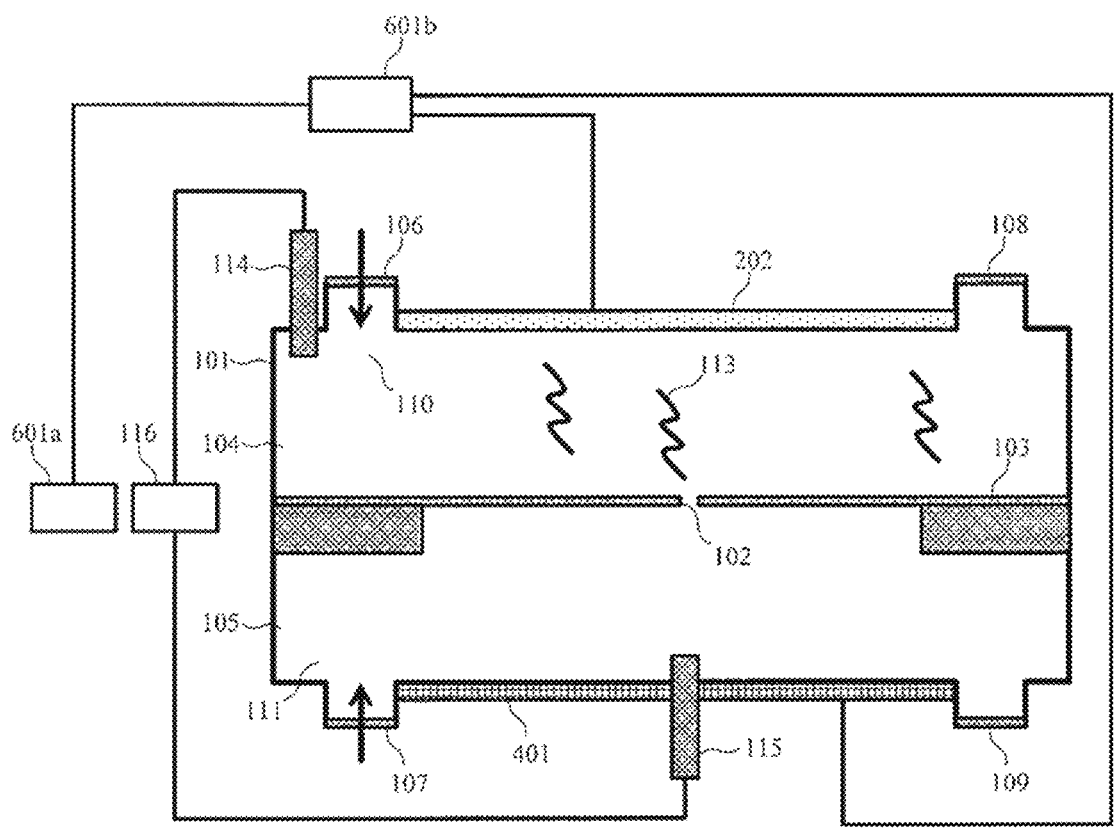

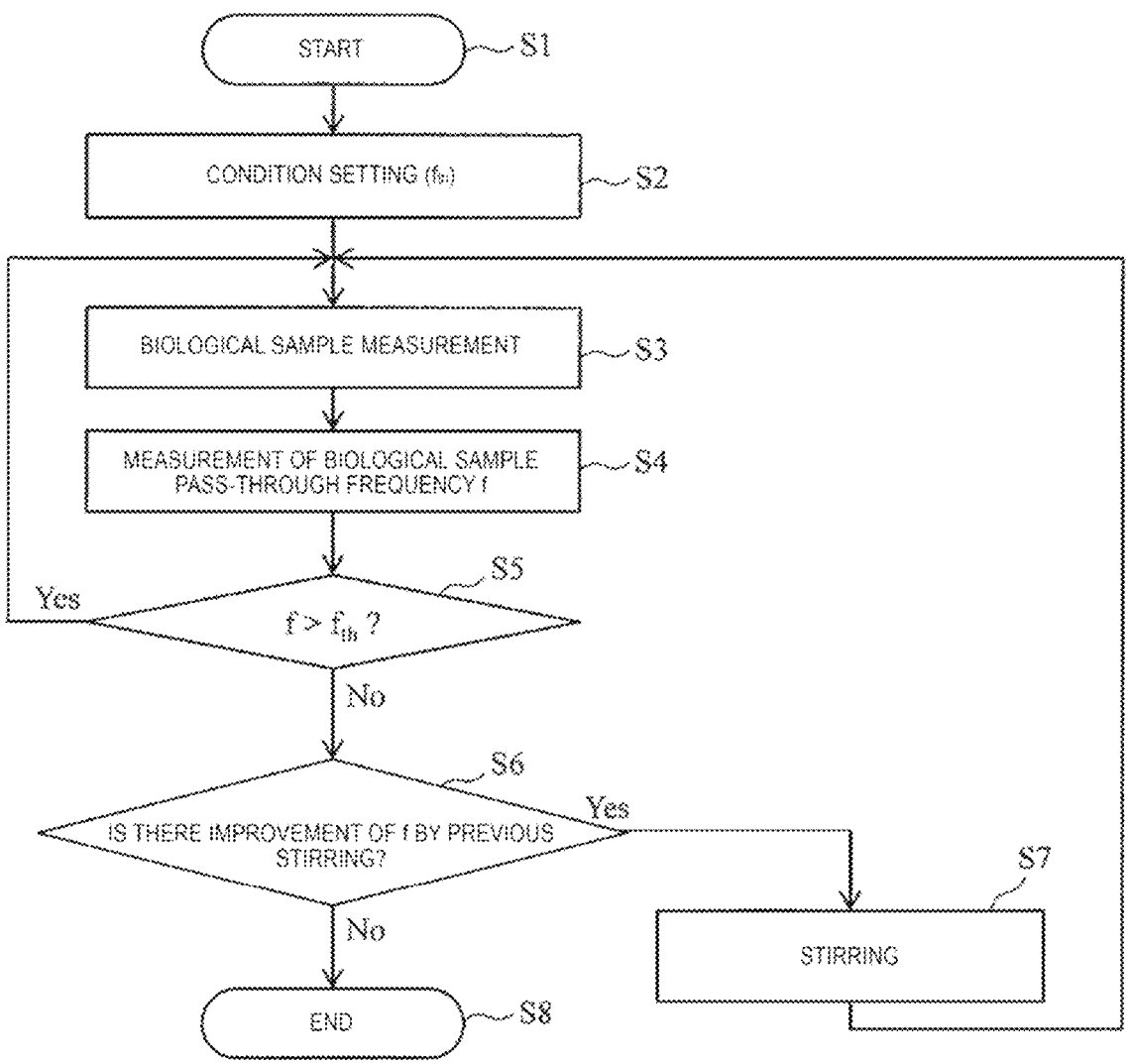

[Fig. 7]
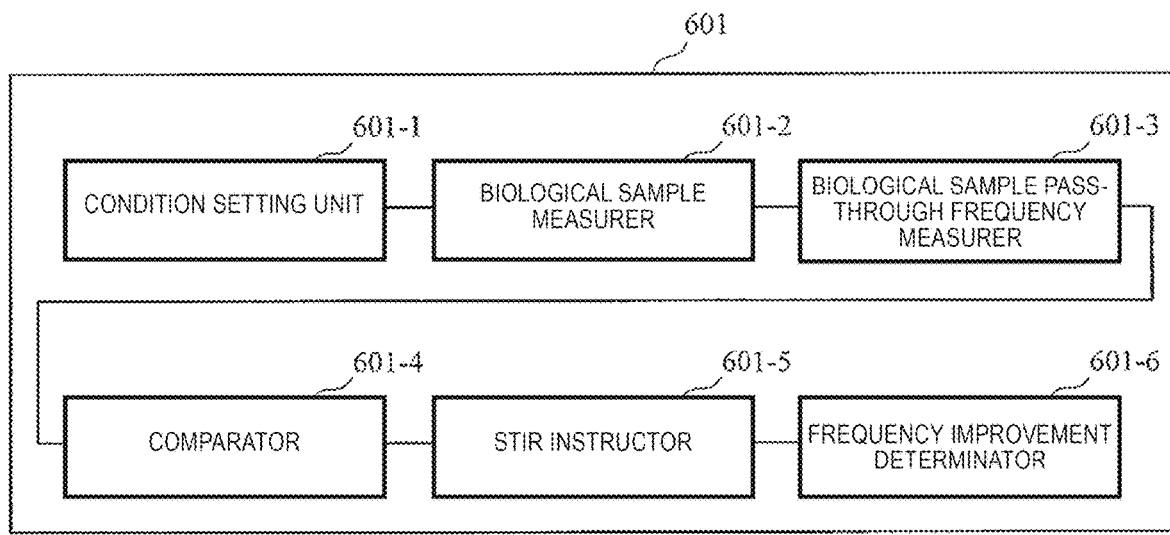
[Fig. 8]
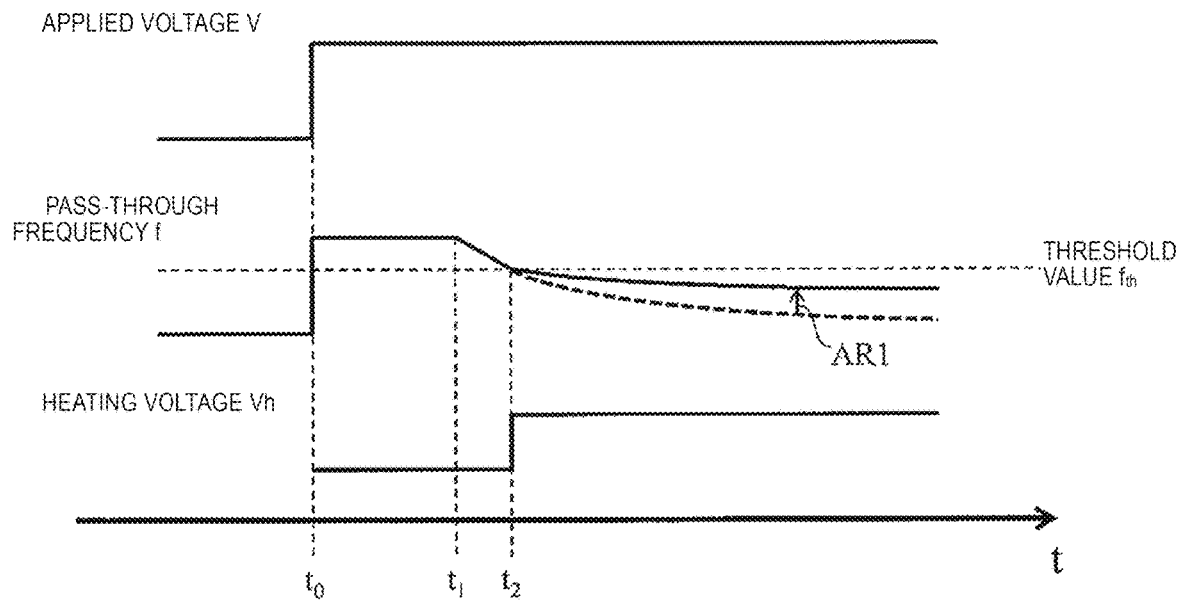

BIOLOGICAL SAMPLE ANALYZER AND BIOLOGICAL SAMPLE ANALYSIS METHOD

TECHNICAL FIELD

The present invention relates to a biological sample analyzer and a biological sample analysis method.

BACKGROUND ART

Analysis of a biological sample, for example, nucleic acid base sequence, is extremely demanded recently for the purpose of detecting causative genes of genetic diseases, evaluating the efficacy and side effects of drugs, detecting gene mutations associated with cancer disease, and the like. The nucleic acid base sequence is analyzed by using a fluorescence detection apparatus (3500 Genetic Analyzer, manufactured by Thermo Fisher Scientific Co., Ltd.) performing capillary electrophoresis, an apparatus (HiSeq 2500 manufactured by Illumina Inc.) for fluorescence detection of a nucleic acid immobilized on a flat plate, and the like.

In these technologies of the related art, it is necessary to use an apparatus having an expensive optical function for performing the fluorescence detection.

As a cheaper detection method, attempts to electrically detect the nucleic acid base sequences are performed. For example, a hole (nanopore) of several nm is manufactured in a thin film of 1 mn to 60 nm by a transmission electron microscope or the like, a liquid tank filled with electrolyte solution is provided on both sides of the thin film, and when an electrode is provided in each liquid tank and a voltage is applied between the electrodes, an ion current flows through the nanopore. The ion current is proportional to the cross-sectional area of the nanopore as a first approximation. When DNA passes through the nanopore, since DNA blocks the nanopore and the effective cross-section decreases, the ion current decreases. This decreased amount is called as a blocking current. Based on the magnitude of the blocking current, there is a method of discriminating the difference between a single strand and double strands of DNA, and a type of base. It is not limited to DNA that is discriminated by the blocking current. For example, it is used for discriminating the biological samples such as RNA, peptides, proteins, and cells. Since the DNA is negatively charged, it passes through the nanopore toward a positive electrode. Here, since each liquid tank is separated by a thin film and the nanopore, electric field distribution is biased in the vicinity of the nanopore, and the DNA in the vicinity the nanopore is attracted. Therefore, it is necessary to efficiently pass the DNA or the like located farther than the nanopore through the nanopore.

As a biological sample analysis technology, there is JP-T-2014-519823 (hereinafter, referred to as "PTL 1"). In PTL 1, it is described that "ultra-low concentration analyte delivery is demonstrated by binding analytes to membranes where appropriate detectors are present, and this reduces the amount of analyte required for detection by several orders of magnitude."

In addition, there is a US-A-2013/0264206 (hereinafter, referred to as "PTL 2"). According to PTL 2, it is described that biomolecules are guided by moderating bias of electric field by an added electrode. In addition, in NPL 1, a technology for increasing the efficiency of DNA passing through the nanopore by preparing a conductive thin film in the vicinity of the nanopore and performing laser irradiation to generate plasmons is disclosed.

CITATION LIST

Patent Literature

PTL 1: JP-T-2014-519823
PTL 2: US-A-2013/0264206

Non Patent Literature

NPL 1: Francesca Nicoli, Nano Lett. 2014, 14, pp 6,917-6,925.

SUMMARY OF INVENTION

Technical Problem

In a case where a base sequence of DNA is analyzed by using the technology of PTL 1, a pretreatment step in which a hydrophobic linker such as cholesterol is imparted to the DNA as a sample, or the like is required. Therefore, time and labor are increased for preparation before measurement. Furthermore, since the efficiency of a process of providing a hydrophobic linker is not necessarily high, this linker is not attached to all the DNA prepared as the sample, That is, the DNA to which the linker is not added is not attracted to the vicinity of the nanopore and is selected. Furthermore, in order to capture all the DNA captured on the thin film, it is necessary to prepare a plurality of nanopores densely. In this case, the difficulties of manufacturing increase that the necessity of maintaining the strength of the thin film having the nanopores and the limitation of densely arranging a plurality of electrodes or the like for detection as well as the plurality of nanopores occur.

In a case where the base sequence of DNA is analyzed by using the technology of PTL 2, in order to guide the DNA as an analyte, an electrode is provided in addition to detection, but in the case of capturing the DNA in a solution tank, the plurality of electrodes must be prepared. Therefore, the vicinity of the nanopore including the electrode for guiding the DNA becomes complicated such that the difficulty of production increases. Furthermore, it is conceivable that the temperature rise in the vicinity of the nanopore becomes significant due to heat generated from the plurality of electrodes, the Brownian motion of the DNA or the like as the analyte becomes large, and noise at the time of detection increases by the vibration of a detection target.

In a case where the base sequence of DNA is analyzed by using the technology of non-PTL 1, a structure that generates plasmons and laser irradiation are required. There is a problem that the structure for generating the plasmons produces not only a nanometer-sized structure as well as the nanopores, but an expensive electron beam lithography apparatus and very high manufacturing technologies are required for manufacturing the nanopores and structures close to each other. Furthermore, since the laser irradiation requires optical parts such as a laser and a lens, features of a nanopore sequencer as an inexpensive detection method are lost. Furthermore, in order to perform plasmon excitation by laser irradiation, since the temperature rise of the solution tank becomes significant as PTL 2, there are also problems that the Brownian motion of the DNA or the like as the analyte becomes large and the noise at the time of detection increases.

In addition, it is also possible to connect flow paths or the like to each of a cis tank and a trans tank as liquid tanks, and to stir the solution in the liquid tank by using a pump, an orifice, or the like. However, by providing a movable mechanism, there arises a problem that concern of deterioration of reliability and necessity of maintenance due to liquid leakage occur.

The present invention is to increase the pass-through frequency of the biological sample passing through the nanopore in a biological sample analysis technology using the nanopore.

Solution to Problem

According to an aspect of the present invention, there is provided a biological sample analyzer using a nanopore including: a first chamber that stores a solvent; a baseboard including the nanopore through which a biological sample passes; a second chamber that is disposed at a position adjacent to the first chamber via the baseboard, and stores the solvent; a biological sample guider that guides the biological sample from the first chamber to the second chamber; a detector that detects the biological sample passing through the nanopore; and a stirrer that stirs the solvent in the first chamber.

Advantageous Effects of Invention

According to the present invention, it is possible to increase the pass-through frequency of the biological sample passing through the nanopore in a biological sample analysis technology using the nanopore.

BRIEF DESCRIPTION OF DRAWINGS

FIG. 1 is a diagram showing a configuration example of a biological sample analyzer of the present invention according to a first embodiment.

FIG. 2 is a diagram showing a configuration example of a biological sample analyzer according to a second embodiment of the present invention.

FIG. 3 is a diagram showing an example of a numerical hydrodynamic analysis result, in a biological sample analysis technology.

FIG. 4 is a diagram showing a configuration example of a biological sample analyzer according to a modification example of FIG. 2.

FIG. 5 is a diagram showing a configuration example of a biological sample analyzer according to a third embodiment of the present invention.

FIG. 6 is a flowchart showing an example of a process flow according to the third embodiment of the present invention.

FIG. 7 is a functional block diagram showing a configuration example of a measurement controller according to the embodiment.

FIG. 8 is a diagram showing a relationship between an applied voltage to voltage applying means, pass-through frequency, and an applied voltage to an electrode for heating.

DESCRIPTION OF EMBODIMENTS

Hereinafter, a biological sample analysis technology according to an embodiment of the present invention will be described in detail with reference to the drawings.

The biological sample analysis technology according to the embodiment relates to a technology for analyzing nucleic acids such as DNA and RNA, and, in particular, relates to a technology for efficiently passing biopolymers through nanopores.

More specifically, for example, the present invention relates to a technology in which the nucleic acid passes through the nanopores with high frequency for nucleic acid sequencing by a nanopore sequencer, and more specifically, it is a stir technology of a sample solution tank for nucleic acid sequencing by the nanopore sequencer, which generates convection by creating a temperature difference in the solution tank and attracts the nucleic acid to the vicinity of the nanopore.

First Embodiment

First, a first embodiment of the present invention will be described.

(Explanation of Nucleic Acid Molecule Measurement)

FIG. 1 is a diagram showing a configuration example of the biological sample analyzer according to an embodiment of the present invention, and exemplarily shows a sectional configuration of a nanopore baseboard and an observation container in which the nanopore baseboard is disposed.

As described in FIG. 1, an observation container (chamber unit) 101 for biological sample analysis includes two closed spaces, that is, a sample guide section 104 and a sample outflow section 105 separated by a nanopore baseboard (baseboard) 103 having the nanopore 102. The sample guide section 104 and the sample outflow section 105 are opposed to each other at positions adjacent to each other. However, the sample guide section 104 and the sample outflow section 105 communicate with each other through the nanopore 102. The sample guide section 104 and the sample outflow section 105 are filled with liquids 110 and 111 guided via inflow paths 106 and 107 respectively connected to both sections. The liquids 110 and 111 flow out of outflow paths 108 and 103 connected to the sample guide section 104 and the sample outflow section 105. The inflow paths 106 and 107 may be provided at positions adjacent (opposed) to the nanopore baseboard 103 interposed therebetween, but are not limited to this disposition. The outflow paths 108 and 109 may be provided adjacent (opposed) to each other with the nanopore baseboard 103 interposed therebetween, but are not limited to this disposition.

It is preferable that the liquid (solvent) 110 be sample solution including a biological sample 113 to foe an analysis target. The liquid 110 preferably contains a large amount of ions serving as charge carriers (hereinafter, referred to as "ionic liquid"). It is preferable that the liquid 110 include only the ionic liquid in addition to the biological sample. As the ionic liquid, it is preferable that an aqueous solution in which an electrolyte having a high ionization degree is dissolved, and a salt solution such as potassium chloride aqueous solution can be suitably used. The melting point of the liquid (solvent) 110 may be less than 0 degrees.

It is preferable that the biological sample 113 have an electric charge in the ionic liquid. The biological sample 113 is typically a nucleic acid molecule, but it is not limited thereto, and the biological sample such as a peptide and a protein may be used.

In the sample guide section 104 and the sample outflow section 105, for example, electrodes 114 and 115 arranged so as to face each other by interposing the nanopore 102 therebetween are provided. In the present embodiment, the voltage applying means 116 is provided for the electrodes 114 and 115. By applying a voltage to the electrodes 114 and 115, a charged biological sample 113 passes from the sample guide section 104 through the nanopore 102, and moves to the sample outflow section 105. The electrodes 114 and 115 and the voltage applying means 116 configure a biological sample guider such that the charged biological sample 113 passes from the sample guide section 104 through the nanopore 102 and moves to the sample outflow section 105. These configure a blocking current detector (detector). Hereinafter, they are also referred to as the blocking current detectors (detector) 114 and 115.

When the nucleic acid molecule passes through the nanopore, since the flow of ions in the nanopore 102 is blocked, a current reduction (blocking current) occurs. By measuring the magnitude of the blocking current and the duration of the blocking current by known blocking current detectors (detectors) 114 and 115, it is possible to detect the length of individual nucleic acid molecule passing through the nanopore 102. In addition, it is also possible to discriminate a type of each base configuring the nucleic acid molecule.

In FIG. 1, the upper part is set as the sample guide section and the lower part is used as the sample outflow section, but it is also possible to detect the biological sample 113 passing through the nanopore 102 with the lower part as the sample guide section and the upper part as the sample outflow section.

In the present embodiment, furthermore, a stirrer 118 that stirs the liquid 110 in the sample guide section 104 is provided. The stirrer 118 can increase pass-through frequency of the biological sample 113 passing through the nanopore 102 by stirring the liquid 110 in the sample guide section 104 as necessary.

Hereinafter, a container and the nanopore will be described.

(Description of Container)

The container used in the present embodiment includes a nanopore baseboard 103 disposed in the chamber unit 101 and an inside thereof. The nanopore baseboard 103 includes a substrate, a thin film formed on the substrate, and the nanopore 102 which is provided in the thin film and communicates a nucleic acid molecule guide section and a nucleic acid molecule outflow section that are samples, and is disposed between the sample guide section 104 and the sample outflow section 105 of the chamber unit 101. The nanopore baseboard 103 may include an insulating layer. It is preferable that the nanopore baseboard 103 be a solid baseboard. The outer periphery of the inner bottom surface of the second chamber that is the sample outflow section 105 may be rounded.

It is possible to form the nanopore baseboard 103 with a material of an electrical insulator, for example, an inorganic material and an organic material (including a polymer material). As examples of the electrically insulating material configuring the nanopore baseboard 103, there are silicon (silicon), a silicon compound, glass, quartz, polydimethylsiloxane (PDMS), polytetrafluoroethylene (PTFE), polystyrene, polypropylene, and the like. As the silicon compound, there are silicon oxynitrides such as silicon nitride, silicon oxide, and silicon carbide. In particular, the base (substrate) configuring a support portion of the baseboard may be made from any of these materials, but it may be, for example, silicon or a silicon compound.

The size and thickness of the nanopore baseboard 103 are not particularly limited as long as the nanopore 102 can be provided. The nanopore baseboard 103 can be produced by a method known in the art, or it can be obtained as a commercial product. For example, the nanopore baseboard 103 can be fabricated by using technologies such as photolithography, electron beam lithography, etching, laser blowing, injection molding, casting, molecular beam epitaxy, chemical vapor deposition (CVD), dielectric breakdown, electron beam, and focused ion beam. The nanopore baseboard 103 may be coated to avoid adsorption of off-target molecules to a surface.

The nanopore baseboard 103 includes at least one nanopore 102. Specifically, the nanopore 102 is provided in a thin film, but in some cases, the nanopore 102 may be provided on the base (substrate) and an insulator at the same time. In the present embodiment, the "nanopore" and a "pore" are pores with a nanometer (nm) size (that is, diameter equal to or greater than 1 nm and less than 1 μm), and communicate the sample guide section and the sample outflow section by penetrating the nanopore baseboard 103.

It is preferable that the nanopore baseboard 103 include the thin film for providing the nanopore 102. That is, by forming the thin film having a material and a thickness suitable for forming nano-sized pores on the baseboard, it is possible to easily and efficiently provide the nanopore 102 on the baseboard 103. From the viewpoint of nanopore formation, it is preferable that the material of the thin film be, for example, graphene, silicon oxide ($SiO_2$), silicon nitride (SiN), silicon oxynitride (SiON), metal oxide, and metal silicate. In addition, the thin film (and possibly the entire baseboard) may foe substantially transparent. Here, the "substantially transparent" means that external light can be transmitted by approximately 50% or more, preferably 80% or more. In addition, the thin film may be a single layer or multiple layers. The thickness of the thin film is 0.1 nm to 200 nm, preferably 0.1 nm to 50 nm, and more preferably 0.1 nm to 20 nm. The thin film can be formed on the baseboard by a known technology in the art, by, for example, low-pressure chemical vapor deposition (LPCVD).

The insulating layer may be provided on the thin film. The thickness of the insulating layer is preferably 5 nm to 50 nm. Although any insulating material can be used for the insulating layer, it is preferable to use, for example, silicon or a silicon compound (silicon nitride, silicon oxide, or the like). In the present embodiment, an "opening" of the nanopore or pore refers to an opening circle of the nanopore or pore of a portion of the nanopore or pore in contact with the sample solution. At the time of analysis of biomacromolecule, the biopolymer, ions, and the like in the sample solution enter the nanopore 102 from one opening and go out of the nanopore 102 from the same or opposite opening.

(Description of Nanopore)

As for the size of the nanopore 102, an appropriate size can be selected according to a type of the biomacromolecule of the analysis target. The nanopore 102 may have a uniform diameter, but it may have different diameters depending on its portion. The nanopore 102 may be connected to a pore having a diameter equal to or greater than 1 μm.

It is preferable that the nanopore 102 provided in the thin film of the nanopore baseboard 103 have a minimum diameter portion, that is, the smallest diameter of the nanopore 102 is 100 nm or less, for example, 1 nm to 100 nm, preferably 1 nm to 50 nm, for example, 1 nm to 10 nm, and, specifically, 1 nm or more and 5 nm or less, 3 nm or more and 5 nm or less, or the like.

The diameter of ssDNA (single-stranded DNA) is approximately 1.5 nm, and an appropriate range of nanopore diameter for analyzing the ssDNA is approximately 1.5 nm to 10 nm, and preferably approximately 1.5 nm to 2.5 nm. The diameter of dsDNA (double-stranded DNA) is approximately 2.6 nm, and an appropriate range of nanopore diameter for analyzing the dsDNA is approximately 3 nm to 10 nm, and preferably approximately 3 nm to 5 nm. Similar to a case where other biomacromolecules such as proteins, polypeptides, and sugar chains are to be the analysis target, the nanopore diameter corresponding to an outer diameter size of the biopolymer can be selected.

The depth (length) of the nanopore 102 can be adjusted by adjusting the baseboard 103 or the thickness of the thin film of the baseboard 103. It is preferable that the depth of the nanopore 102 be a monomer unit configuring the biomacromolecule of the analysis target. For example, in a case where the nucleic acid as the biomacromolecule is selected, it is preferable that the depth of the nanopore 102 be equal to or less than one base, for example, approximately equal to or less than 0.3 nm. A shape of the nanopore 102 is basically a circular shape, but it may be an oval shape or a polygonal shape.

It is possible to provide at least one nanopore 102 on the baseboard 103, and in a case where the plurality of nanopores 102 are provided, they may be arranged regularly. The nanopore 102 can be formed by a method known in the art, for example, by irradiating with an electron beam of a transmission electron microscope (TEM), by using a nanolithography technology, an ion beam lithography technology, or the like. The nanopore 102 may be formed on the baseboard by dielectric breakdown.

The chamber unit 101 includes the sample guide section 104, the sample outflow section 105, the nanopore baseboard 103, the electrodes 114 and 115, the electrode for passing the biological sample 113 through the nanopore 102, and the like. In the preferred example, the chamber unit 101 includes the sample guide section 104, the sample outflow section 105, a first electrode 114 provided in the sample guide section 104, a second electrode 115 provided in the sample outflow section 105, the voltage applying means 116 with respect to the first and second electrodes, and the like. An ammeter may be disposed between the first electrode 114 provided in the sample guide section 104 and the second electrode 115 provided in the sample outflow section 105. A current between the first electrode 114 and the second electrode 115 may be appropriately determined in determining nanopore pass-through velocity of the sample. For example, in a case where an ionic liquid not containing the sample is used, it is preferably that it be approximately 100 mV to 300 mV in a case of the DNA, but the value is not limited to this value.

The electrodes can be made of metals, for example, platinum group such as platinum, palladium, rhodium, ruthenium, gold, silver, copper, aluminum, and nickel; graphite, for example, grapheme (which may be single layer or multiple layers), tungsten, and tantalum.

A biological sample (nucleic acid molecule) 113 passing through the nanopore 102 by voltage application emits Raman light by excitation light, but a conductive thin film may be prepared in the vicinity of the nanopore and a near field may be generated and reinforced. It is also possible to increase not only the blocking current but also base determination accuracy by adding information obtained from the Raman light. As is clear from the definition of the thin film, the conductive thin film disposed in the vicinity of the nanopore is formed in a planar shape. A thickness of the conductive thin film is set to 0.1 nm to 10 nm, preferably, 0.1 nm to 7 nm depending on the material adopted. As the thickness of the conductive thin film is small, the generated near field can be limited, and analysis with high resolution and high sensitivity becomes possible. In addition, the size of the conductive thin film is not particularly limited, and can be appropriately selected according to the size of the solid baseboard and the nanopore to be used, the wavelength of the excitation light to be used, or the like. Mien the conductive thin film is not planar and bending or the like present therein, the near field is induced at a bent portion thereof, light energy leaks, and Raman scattered light is generated at a location outside the target. That is, background light increases and S/N decreases. Therefore, it is preferable that the conductive thin film have a planar shape, in other words, it is preferable that the cross-sectional shape be a linear shape without bending. It is preferable that forming the conductive thin film in a planar shape be effective not only for reducing the background light and for increasing an S/N ratio, but also from the viewpoint, of uniformity, reproducibility in fabrication, and the like of the thin film.

Second Embodiment

Next, the second embodiment of the present invention will be described. In the present embodiment, as the stirrer 118 in the first embodiment, a configuration as shown in FIG. 2 is used.

That is, in the present embodiment, as an example of the stirrer 118 that performs stirring of the liquid 110 to which the biological sample 113 is input, using convection, in order to pass the nucleic acid molecule that is the biological sample 113 with high frequency through the nanopore 102, the stirrer 118 convects the solution in the sample guide section 104 by heating a heater 201 provided on an upper surface of the sample guide section 105. For example, the heater 201 may be provided on a surface opposite to the sample outflow section 105 of the sample guide section 104.

By heating the liquid 110 to which the biological sample 113 is input through the heater 201, the temperature in the sample guide section 104 rises, the Brownian motion of the nucleic acid molecule increases, and the pass-through frequency of the biological sample 113 increases.

However, by heating, the temperature in the sample guide section 104 rises and the Brownian motion of the nucleic acid molecule increases. In a case where above conditions become noise in the measurement of a blocking current passing through the nanopore 102, a temperature difference in the sample guide section 104 is created by cooling by a cooler 202 such that Benard convection which is gentle convention may be generated. The Benard convention is a phenomenon in which a liquid layer is divided into a cellular vortex region in a substantially regular hexagon shape, and a flow is generated in which the flow is upward in the central portion and downward in the peripheral portion, if temperature gradient exceeds a certain critical value when a horizontal liquid layer is heated from below or cooled from above to give upper and lower temperature gradients. Rayleigh number $Ra_L$ is guided as a dimensionless number that dominates this phenomenon, and in a state where $Ra_L$ slightly exceeds a critical value Rac, cellular vortex regions of approximately the same size of four to six hexagons appear on one surface, but when the $Ra_L$ increases, the cellular vortex regions continue in one row to form a parallel band structure. The band structure is formed with a roll-shaped vortex alternately rotating inversely, and $Ra_L$ is kept stable until $Ra_L$ becomes approximately 10 times Rac, but it is known that when it exceeds it, it collapses and the convection becomes a turbulent state, and when the Rayleigh number $Ra_L$ is equal to or greater than 1,710, a Benard cell is formed and the convection occurs.

$$Ra_L = \frac{g\beta(T_1 - T_2)L^3}{v\alpha} \qquad \text{[Equation 1]}$$

Here, the parameters are as follows,
g: gravitational acceleration
β: body expansion coefficient
V: kinematic viscosity coefficient
α: thermal diffusivity
L: distance between high-temperature part ($T_1$) and low-temperature part ($T_2$)

For example, when water is used as a solvent in the configuration of FIG. 2, L=1 mm and a temperature difference of 10 K, $Ra_L$=2,604 is reached, convection that forms a Benard cell occurs, and the sample in the sample guide section 104 can be stirred. FIG. 3 shows results (CD-adapco analysis software STAR-CCM+used) obtained by performing computational fluid dynamics in a case where temperature control with the cooler 202 fixed at a temperature of 25° C. is performed. As shown in FIG. 3, it can be seen that the Benard cell is formed from a temperature difference of approximately 10° C. and the solution in the sample guide section 104 is stirred. As the temperature difference increases, the formation of the Benard cell becomes active, the temperature difference for analysis becomes turbulent in the vicinity of 17° C., and active stirring is performed. Therefore, it can be seen that the heater 201 and the cooler 202 operate as a stirring mechanism. It is noted that the data in the right column of FIG. 3 depicts streamlines by using the line integral convolution method (Line Integral Convolution LIC).

This phenomenon that the convection occurs only by the temperature difference, may be used. In a case where the Brownian motion in which the vibration of molecules as the biological sample 113 is dependent on heat influences the measurement, it is also possible to perform stirring of the biological sample 113 by causing the convection at low temperature in order to reduce the vibration. As a charge supply source, potassium chloride, lithium chloride, or the like is selected, and blocking current measurement is generally performed by using water as the solvent. But, under this solution condition, freezing occurs equal to or less than 0° C. For example, by using a solvent with a low freezing point such as ethanol and acetone and making a temperature difference at a low temperature equal to or less than 0° C., the Brownian motion is suppressed and measurement with reduced noise maybe performed.

In FIG. 2, the heater 201 is disposed below the nanopore baseboard 103, but, for example, it. may be disposed on the side of the sample guide section 104. That is, the heater 201 may be disposed at a position where the convection occurs due to a temperature difference and the sample moves in the vicinity of the nanopore 102 by the convection. For example, as described in FIG. 4, a heater 401 is installed downward the sample outflow section 105, and by increasing temperature in the sample outflow section 105, the bottom of the sample guide section 104 is overheated to create a temperature difference between the top and the bottom of the sample guide section 104 such that the convection may occur. In order to control the temperature difference properly and to control the convection, a temperature sensor may be provided at the upper part or the lower part of the tank where it is desired to generate the convection. Furthermore, the temperature sensor may foe provided for correctly controlling the temperature of the heater 201 and the cooler 202. For example, the cooler 202 may be cooled by using a Peltier device or the like, but it is not necessary to prepare a device for cooling, heating may be performed in the heater 201 so as to appropriately set this room temperature state to a value detected by the temperature sensor in a room temperature state in which a container is installed such that the temperature difference is generated. The efficiency of stirring may be increased by curving the corner portion of the container or the like.

Third Embodiment

In a third embodiment of the present invention, instead of stirring the biological sample constantly by using the convection during the measurement, a measurement container which can measure the pass-through efficiency of the biological sample and can stir the solution containing the biological sample when the pass-through frequency decreases, is used.

FIG. 5 is a diagram showing a configuration example of a measuring device 500 in the present embodiment.

In the second embodiment, the convection is generated by applying heat to the liquid. Meanwhile, in the present embodiment, in a case where the measurement is affected such as excessive heat or force is applied to the biological sample 113 under measurement and the biological sample 113 itself is not filled into the nanopore 102 due to vibrations of the biological sample 113 itself or fast convection, it is possible to reduce the influence.

While measuring the biological sample 113, for example, the pass-through frequency of the nanopore 102 of the biological sample 113 within a certain period of time is also measured as, for example, an electrical signal value. Then, when the pass-through frequency is equal to or less than the expected pass-through frequency (threshold value $f_{th}$), a stir operation is performed. As the stir operation, in a case of a configuration shown in FIG. 5 as an example of the stir operation, the temperature control between the heater 401 and the cooler 202 may be performed, and stirring may be performed by the convection due to a temperature difference. In a case where the Brownian motion due to residual heat affects the measurement when heating for the purpose of stirring is performed, the measurement may be started after the solution is once cooled by using a cooling mechanism after the stirring. As described above, in the present embodiment, the biological sample guiders (114, 115, and 116) and the stirrers (for example, 202 and 401) are provided and they can be controlled independently such that it is possible to effectively detect the biological sample 113, In an example shown in FIG. 5, the measurement controller 601 includes a measurer 601a that measures the pass-through frequency and a controller 601b that performs temperature control based on the pass-through frequency.

FIG. 6 is a flowchart showing an example of a process flow according to the present embodiment. FIG. 7 is a functional block diagram showing a configuration example of a processing unit of performing a process. FIG. 3 is a diagram showing an example of a control state.

As described in FIG. 7, the measurement controller 601 according to the present embodiment, for example, a condition setting unit 601-1, a biological sample (nucleic acid molecule) measurer 601-2, a biological sample (nucleic acid molecule) pass-through frequency measurer 601-3, a comparator 601-4, a stir instructor 601-5, and a frequency improvement determinator 601-6. For example, the blocking current detectors (detector) 114 and 115 may include the measurer 601a or a biological sample (nucleic acid molecule) measurer 601-2. In addition, the biological sample may be detected by a method other than measurement of the blocking current or a method in which other methods are added to the blocking current.

As described in FIG. 6, first, the condition setting unit 601-1 sets measurement conditions (step S1). However, in general, as a detection condition of the biological sample 113, for example, not only a discrimination condition of blocking signal values of various bases such as DNA, but also conditions for stirring or the like are set in a memory or the like.

Here, the condition setting for stirring is, for example, the setting of a threshold value $f_{th}$ of the pass-through frequency which is a trigger for starting the stirring. In a case where the frequency of the biological sample 113 passing through in a certain period of time decreases, the stirring is started. For example, based on the current value in a state where the biological sample 113 does not pass through the nanopore 102, the biological sample 113 enters the nanopore 102, the pore is sealed, a current value becomes small, it is detected that the biological sample 113 passes through the nanopore 102 and returns to the original current value, thereby passing through the nanopore 102, and the frequency per hour is obtained and counted, such that the pass-through frequency is obtained.

Since an absolute number of the biological sample 113 decreases with the elapse of the measurement time, a condition that the threshold value $f_{th}$ of the pass-through frequency changes with the measurement time may foe given. In a case of a measurement container having the plurality of nanopores 102, since it is not preferable for many nanopores 102 to shift to the stir operation during measurement when influencing measurement, the ratio of the number of nanopores under the measurement may be used as a threshold value. In a case where the biological sample 113 and impurities in the solution are clogged in the nanopore 102 and a state where the current value is always constant and blocked is indicated such that the measurement becomes impossible, the stirring may be performed by the stirrer 118 (heater 401, cooler 202, and the like may be used) to eliminate the clogging of the nanopore 102, and the ratio of the number of nanopores under measurement among the plurality of nanopores 102 may be set to a threshold value. In addition, in a case the length of the base being read is long (for example, equal to or greater than 20 kbp) and the measurement is in progress while DNA that is the biological sample 113 passes through the nanopore 102 before moving to the stir operation, settings that the measurement is continuously performed may be performed.

Furthermore, the intensity of the convection may be set as a condition of the stirring. For example, the temperatures of the heater 201 and the cooler 202 may be set individually. Turbulent flow may be generated by increasing the temperature difference to be set and the stirring may be performed in a short time or a condition causing loose convection that does not affect, the measurement may be set. Since setting of these temperatures changes a condition of the convection depending on a type of the solvent and a shape of the container, setting taking each condition into consideration is performed.

In step S3, a biological sample measurer 601-2 performs various measurements relating to the biological sample. In addition, in step S3, a biological sample pass-through frequency measurer 601-3 measures frequency f of the biological sample 113 passing through the nanopore 102. The biological sample measurer 601-2 and the biological sample pass-through frequency measurer 601-3 may be integrated.

In step S5, the comparator 601-4 performs comparison of measured f and $f_{th}$. Therefore, in a case of $f > f_{th}$ (Yes), the process returns to step S3. In a case of $f <= f_{th}$ (No), the process proceeds to step S6, and the frequency improvement determinator 601-6 determinates whether or not there is an improvement effect of f by the previous stirring. In step S6, in a case of Yes, the process proceeds to step S7, the stir instructor 601-5 instructs the stir operation with respect to the stirrer 113, and the process returns to step S3. In a case of No in step S6, the process ends (step S8).

As described in FIG. 8, at a certain timing $t_0$, when a voltage is applied to the voltage applying means 116 between the electrodes 114 and 115 of (a), a transmission frequency f of the biological sample 113 increases, Therefore, after a certain period of time ($t_1$), the decrease of the transmission frequency f due to clogging of the sample in the nanopore is seen (see broken line). For example, when the f measured in the plurality of nanopores is lower than a threshold value $f_{th}$, for example, the stirring is performed at the timing or a subsequent timing $t_2$. In this example, a heating voltage Vh is applied.

Then, the convection occurs in the liquid, as indicated by an arrow AR1, the improvement of the pass-through frequency f is seen. For example, by performing continuously such control, it is possible to efficiently transmit the biological sample 113 through the nanopore 102, and it is possible to smoothly perform the measurement of the biological sample.

In the condition setting unit 601-1, even after the stirring, in a case where the pass-through frequency is not improved, a condition such as the number of times of the stirring again may be set. Measurement after setting of a condition and measurement of the pass-through frequency are performed, and a process performing repeatedly an operation of the stirring when the pass-through frequency decreases, is performed. However, in a case where a desired pass-through frequency is not acquired even in a case of repeating the stirring, the measurement may be ended. The setting conditions shown here are only examples, and not limited thereto.

However, an operation of causing the stirring, the example in which the convection is caused by the temperature difference is described above, but the present invention is not limited thereto. That is, when the stir operation accompanies the measurement operation, in a case where measuring data is adversely affected, measurement operation and stirring operation can be applied separately.

For example, means for mitigating the bias of the electric field capturing the biological sample 113, and for stirring the solution in the sample guide section 104 so as to guide the biological sample 113 in the vicinity of the nanopore, by separately adding an electrode in the container, means for providing the near field in the vicinity of the nanopore and stirring the solution by laser irradiation, and means for directly stirring the biological sample 113 by moving the solution in the sample guide section 104 by a pump, an orifice, a stirrer, a pipette operation, or the like, may be also used.

A biological sample capturing technology of the present invention has the following effects.

Since improvement in the nanopore pass-through efficiency of the biological sample contained in a liquid tank by temperature control does not require a special reaction process for the biological sample, there is an effect of reducing the work burden of an analyst.

Furthermore, since it is possible to transport all the biological samples in the liquid tank to the vicinity of the nanopore and a sample located at a position separated from the nanopore is attracted without selecting the sample in the solvent in the liquid tank, it is possible to positively pass through the nanopore.

For example, in a case where multiple tests are performed on the biological samples, which are clinical specimens, from various angles, it is necessary to secure a sufficient amount of sample in order to separate the samples for each test. However, it is sometimes difficult to collect a large number of samples such as blood from a child or a serious patient, but such a problem can be solved.

In addition, since temperature management from the outside of the solution tank is also possible, there is no limitation on electrode installation and a nanopore installation interval, and a precision process for the pass-through efficiency is not required.

In addition, since the convection is generated by the temperature difference, it. becomes possible to reduce noise when detecting by the Brownian motion of the sample at the time of detection.

Process and control can be realized by a software process by a central processing unit (CPU) or a graphics processing unit (GPU), and by a hardware process by an application specific integrated circuit (ASIC) or a field programmable gate array (FPGA).

In the above-described embodiments, the configurations and the like illustrated in the accompanying drawings are not limited thereto, and can foe appropriately changed within a range that exerts the effects of the present invention. Besides, as long as it does not deviate from a scope of an object of the present invention, and it is possible to carry out it by appropriately changing it.

In addition, each configuration element of the present-invention can arbitrarily be selected and sorted out, and an invention having a configuration which is selected and discriminated is also included in the present invention.

REFERENCE SIGNS LIST

101: observation container (chamber unit)
102: nanopore
103: nanopore baseboard (baseboard)
104: sample guide section (first chamber)
105: sample outflow section (second chamber)
106, 107: inflow path
108, 109: outflow path
110, 111: liquid
113: biological sample
116: voltage applying means (biological sample guider)
114, 115: electrode (biological sample guider), detector (blocking current detector)
118: stirrer
201: heater
202: cooler
401: heater
403a, 403b, 403c, 403d: temperature sensor
500: measuring device
601: measurement controller
601-1: condition setting unit
601-2: biological sample (nucleic acid molecule) measurer
601-3: biological sample (nucleic acid molecule) pass-through frequency measurer
601-4: comparator
601-5: stir instructor
601-6: frequency improvement determinator All publications, patents and patent applications cited in this specification are incorporated herein by reference in their entirety.

The invention claimed is:

1. A biological sample analyzer using a nanopore, comprising:
a first chamber that stores a solvent;
a baseboard including the nanopore through which a biological sample passes;
a heater disposed on a lower surface of the baseboard;
a cooler disposed on an upper surface of the first chamber;
a second chamber that is disposed at a position adjacent to the first chamber via the baseboard, and stores the solvent;
a biological sample guider that guides the biological sample from the first chamber to the second chamber; and
a detector that detects the biological sample passing through the nanopore,
wherein the biological sample guider guides the biological sample to the nanopore by Benard convection on the solvent in the first chamber,
wherein the detector is configured to measure a pass-through frequency of the biological sample passing through the nanopore, and
wherein a high temperature part of the Benard convection is 42° C. or less.

2. The biological sample analyzer according to claim 1, further comprising:
a controller that controls guidance of the biological sample to the nanopore by the Benard convection based on a detected result by the detector.

3. The biological sample analyzer according to claim 1, wherein guidance of the biological sample to the nanopore by the Benard convection is controlled by the following expression, $$5 < RaL < 1{,}710 \text{ where, } Ra_L = \frac{g\beta(T_1 - T_2)L^3}{v\alpha}$$

here, the parameters are as follows.
g: gravitational acceleration
β: body expansion coefficient
V: kinematic viscosity coefficient
α: thermal diffusivity
L: distance between heater and cooler
$T_1$: solution temperature of the upper portion of the first chamber
$T_2$: solution temperature of the lower portion of the second chamber.

4. The biological sample analyzer according to claim 2, wherein the controller controls a timing at which the biological sample is guided to the nanopore by the Benard convection, based on the detected result of the detector.

5. The biological sample analyzer according to claim 4, wherein the biological sample is guided to the nanopore by the Benard convection in a case where the pass-through frequency is equal to or less than a predetermined value.

6. The biological sample analyzer according to claim 1, wherein an outer periphery of an inner bottom surface of the second chamber is rounded.

7. The biological sample analyzer according to claim 1, wherein a melting point of the solvent is less than 0° C.

8. The biological sample analyzer according to claim 1, further comprising:
   a first temperature sensor that measures a temperature of an upper portion of the first chamber.

9. The biological sample analyzer according to claim 1, further comprising:
   a second temperature sensor that measures a temperature of a lower portion of the first chamber.

10. The biological sample analyzer according to claim 1, wherein the biological sample guider includes first and second electrodes, the first electrode being disposed in the first chamber adjacent to an inflow path of the first chamber, and the second electrode being disposed in the second chamber at a position directly across from the nanopore.

11. A biological sample analysis method using a nanopore comprising:
   a step of guiding a biological sample from a first chamber in which a solvent is stored, to a second chamber which is disposed at a position at which the biological sample passes through the nanopore through which the biological sample can pass and which is adjacent to the first chamber, and in which the solvent is stored;
   a step of detecting, by a detector, the biological sample passing through the nanopore,
   wherein in the step of guiding the biological sample, the biological sample is guided to the nanopore by Benard convection on the solvent in the first chamber, based on a heater disposed on a lower surface of the first chamber and a cooler disposed on an upper surface of the first chamber,
   wherein the detector is configured to measure a pass-through frequency of the biological sample passing through the nanopore, and
   wherein a high temperature part of the Benard convection is 42° C. or less.

12. The biological sample analysis method according to claim 11,
   wherein the biological sample is guided from the first chamber to the second chamber by a biological sample guider that includes first and second electrodes, the first electrode being disposed in the first chamber adjacent to an inflow path of the first chamber, and the second electrode being disposed in the second chamber at a position directly across from the nanopore.

* * * * *